United States Patent [19]

Ling et al.

[11] 4,409,139

[45] Oct. 11, 1983

[54] GONADOSTATIN

[75] Inventors: Nicholas C. Ling, San Diego; Roger C. L. Guillemin, La Jolla; Shao-Yao Ying, San Diego; Frederick S. Esch, Oceanside, all of Calif.

[73] Assignee: The Salk Institute for Biological Studies, San Diego, Calif.

[21] Appl. No.: 291,294

[22] Filed: Aug. 10, 1981

[51] Int. Cl.³ ............................................. C07G 15/00
[52] U.S. Cl. ........................ 260/112 R; 260/112.5 LH
[58] Field of Search .................... 424/105; 260/112 R, 260/112.5 LH

[56] References Cited

PUBLICATIONS

Franchimont P. et al., *Vitamins and Hormones*, vol. 37, 1979, pp. 243-302.
De Jong and Sharpe, Nature, vol. 263, pp. 71-72, 1976.
Steinberger and Steinberger, Endocrinology 99: 918-921, 1976.
Chari S. et al., Acta Endocrinologica 87: 434-448, 1976.
Franchimont et al., Nature, vol. 257, pp. 402-404, 1975.
De Jong et al., J. Endocrinology 80: 91-102, 1979.
Ying et al., Bioregulators of Reproduction, pp. 389-401, 1981.

*Primary Examiner*—Allan Lieberman
*Assistant Examiner*—Patricia Short
*Attorney, Agent, or Firm*—Fitch, Even, Tabin & Flannery

[57] ABSTRACT

A substantially purified substance has been isolated from bovine gonadal secretions which mediates pituitary hormone secretion, using an extraction and purification sequence that includes gel filtration, partition chromatography and HPLC in that order. The substance, designated gonadostatin, is a moderate-size peptide which below a threshold level selectively inhibits LRF-stimulated pituitary secretion of LH and FSH. Above a threshold level, gonadostatin generally stimulates pituitary hormone secretion.

5 Claims, 4 Drawing Figures

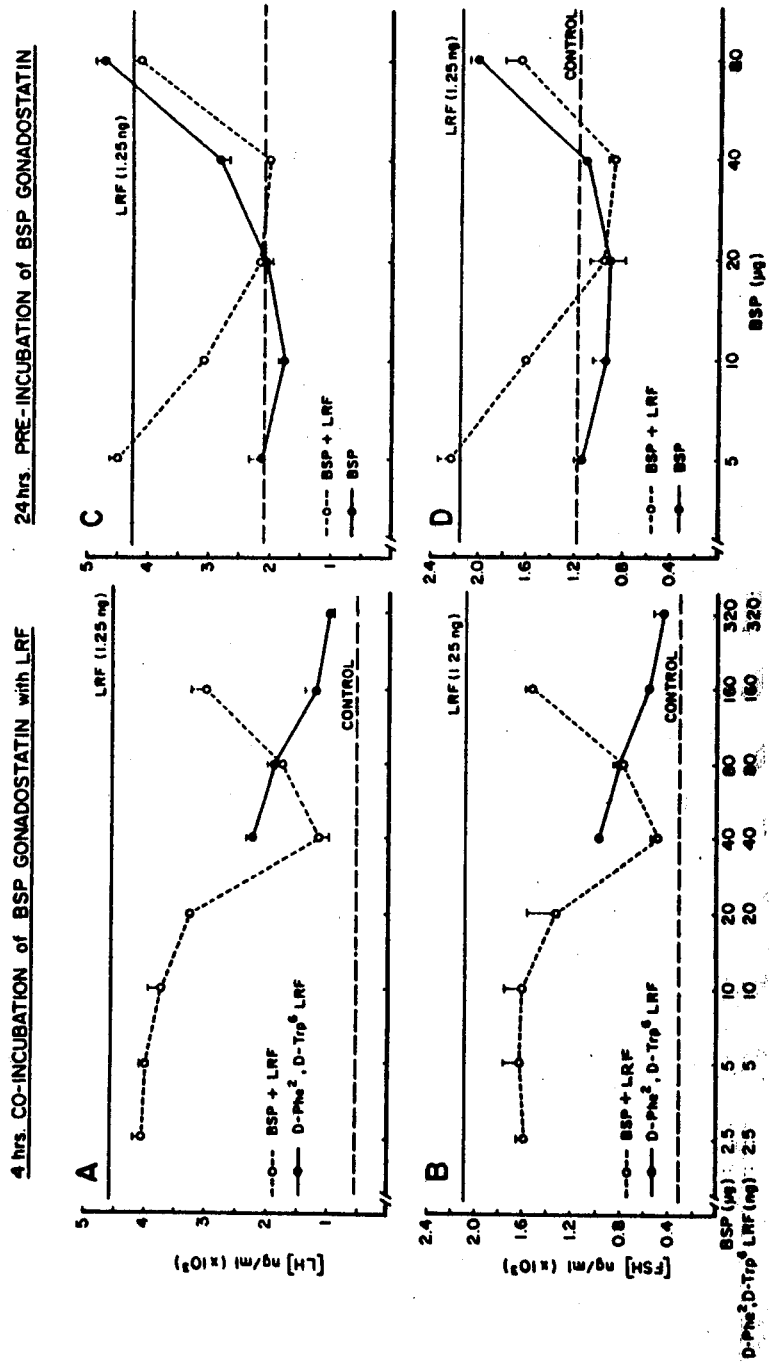

GONADOSTATIN

The present invention relates to peptides which influence the release of hormones by the anterior pituitary gland.

BACKGROUND OF THE INVENTION

The pituitary gland is attached by a stalk to the region in the base of the brain known as the hypothalamus. The pituitary gland has two lobes, the anterior and posterior lobes. The posterior lobe of the pituitary gland stores and passes onto the general circulation two hormones manufactured in the hypothalamus, these being vasopressin and oxytocin. The anterior lobe of the pituitary gland secretes a number of hormones, which are complex protein or glyco-protein molecules that travel through the blood stream to various organs which, in turn, stimulate the secretion into the blood stream of other hormones from the peripheral organs. In particular, follicle stimulating hormones (FSH) and luteinizing hormone (LH) are released by the anterior pituitary gland. These hormones, in combination, regulate the functioning of the gonads to produce testosterone in the testis and progesterone and estrogen in the ovaries, as well as regulating the production and maturation of gametes. These hormones are sometimes referred to as gonadotropins or gonadotropic hormones. The release of a hormone by the anterior lobe of the pituitary gland usually requires a prior release of another class of hormones produced by the hypothalamus. One of the hypothalamic hormones acts as a factor that triggers the release of the gonadotropic hormones, namely, LH and FSH, and has been designated luteinizing hormone releasing factor (LRF) or LH-RH or GnRH.

It has long been felt that a mechanism may operate whereby hormones produced by the gonads would, by a feedback loop, regulate the secretion of gonadotropins by the pituitary gland. Such a mechanism was originally proposed by D. R. McCullagh in 1932, (*Science* 76, 19-20). A hypothetical gonadal substance, designated inhibin, which was non-steroidal but proteinaceous in nature was proposed to be released into general circulation and to act specifically on the pituitary gland, selectively inhibiting the secretion of FSH, but not of LH. In recent years, inhibin-like activity, i.e., the selective inhibition of FSH, has been reported in extracts of testis, spermatozoa, rete testis fluid, seminal plasma and ovarian follicular fluid. Other researchers have reported inhibition of the secretion of both LH and FSH by rete testis fluid, seminal plasma, Sertoli cell culture fluid, granulosa cell culture fluid, and follicular fluid. The selective inhibition of LH and FSH release from the LRF-stimulated pituitary by a substance of gonadal origin will be referred to herein as gonadostatin activity, and the gonadal substance which selectively inhibits the stimulated LH and FSH secretion from the pituitary will be referred to as gonadostatin. Although several investigators have observed inhibin and/or gonadostatin activity in crude or partially purified gonadal extracts, none has heretofore isolated and characterized a substance which is responsible for these activities.

SUMMARY OF THE INVENTION

A substantially pure substance, which is primarily protein in nature, has been isolated from mammalian seminal plasma. The substance, designated gonadostatin, selectively inhibits LRF-induced secretions of FSH and LH and has a molecular weight of about 11,000, as measured by gel filtration. The purification of gonadostatin is achieved by gel filtration, followed by partition chromatography, followed by reverse-phase high performance liquid chromatography (HPLC), with selection of fractions exhibiting gonadostatin activity at each step.

DETAILED DESCRIPTION OF THE PREFERRED EMBODIMENT

In accordance with the present invention, a substance, designated gonadostatin, has been isolated from bovine seminal plasma (BSP) which according to HPLC and N-terminal analysis criteria shows a purity greater than 99% by weight. When added to an in vitro culture of rat anterior pituitary cells, gonadostatin, in concentrations of up to about 50 $\mu$g/ml., inhibits LRF-induced pituitary secretion of LH and FSH. Higher doses of gonadostatin generally promote the secretion of pituitary hormones including LH, FSH and TSH.

The isolation of gonadostatin from bovine seminal plasma has been achieved essentially through a three-step chromatography protocol. A precipitate from BSP is first obtained by treatment with 86% ethanol, which is then separated according to molecular weight by gel filtration on a cross-linked polysaccharide column (Sephadex G-75) eluted with 30% acetic acid solution. It is then subjected to partition chromatography with a 1-butanol:pyridine:acetic acid:water buffer system, and finally purified by reverse phase high performance liquid chromatography with a formic acid:pyridine:1-propanol:water buffer system of increasing 1-propanol concentration. The inactivation of gonadostatin by trypsin or chymotrypsin demonstrates the substantially proteinaceous nature of gonadostatin.

Gonadostatin has been found to have no significant effect on thyrotropin releasing factor (TRF)-mediated secretion of either thyrotropin (TSH) or prolactin (PRL). In high amounts, e.g., in amount of 200 $\mu$g/ml., gonadostatin has the effect of stimulating pituitary secretion of LH and FSH, as well as TSH, but the magnitude of TSH release is less than that of LH and FSH. However, secretion of GH, PRL and B-endorphin is not stimulated in any appreciable amount by high doses of gonadostatin.

Gonadostatin activity is determined by a bioassay system which demonstrates inhibition of LRF-induced secretion of LH and FSH using pituitary tissue cultures. A base line level of gonadotropin secretion is determined by measuring the gonadotropin secretion of non-induced pituitary tissue cultured in vitro. The level of gonadotropin secretion induced by a challenge dose of a given amount of LRF is also measured. Gonadostatin activity is demonstrated when administration of the challenge dose of LRF plus a given amount of the substance in question results in a gonadotropin secretion between the base line and the LRF-induced level.

In the in vitro bioassay, LRF plus purified gonadal peptide are co-incubated in a pituitary monolayer culture as described in Ying, S. et al. *Endocrinology* 108, 1206 (1981). Immature female rats are used as the pituitary donors, and multiwell culture plates are used to facilitate the handling of multiple samples for screening numerous fractions. The end-point concentrations of LH and FSH in the culture fluids after four hours incubation with the various treatments are determined by radioimmunoassay using Staphylococcus aureus as a rapid separating agent. As an internal control to assure the responsiveness of the culture system to LRF-inhibition, a known, synthetically produced, LRF antagonist, [D-Phe$^2$, D-Trp$^6$]-LRF is employed.

The purification of gonadostatin and characterization thereof will now be described in greater detail by way of example.

EXAMPLE I

Bovine seminal plasma (BSP) was precipitated in 86% ethanol and the precipitate recovered. The components of the BSP precipitate were first separated, generally according to their molecular weight, on a gel filtration column of highly cross-linked polysaccharide material. A 5×150 cm. column was packed with Sephadex G-75 in 30% acetic acid, equilibrated with 4 l. of 30% acetic acid and calibrated with peptides of known molecular weight. 0.5 gm. of the BSP precipitate, dissolved in about 15 ml. of 30% acetic acid was applied to the column, and fractions of 20 ml. each were collected. For bioassays, 100 µg. of bovine serum albumin (BSA) and 2 ml. of water were added to appropriate aliquots from the column fractions, and the contents lyophilized and reconstituted for assay. Fractions 66–70, contained 111.5 mg. of material which ultimately exhibited gonadostatin activity in the in vitro assay.

About 100 mg. of the partially purified material contained in pooled eluate fractions 66–70 was next subjected to partition chromatography using a 2×102 cm. column of a cross-linked polysaccharide, sold under the tradename Sephadex G-50, which was packed with 0.5 M acetic acid and then equilibrated with 600 ml. of the lower phase of a two-phase solvent system: 1-butanol:pyridine:acetic acid:water (6:4:1:9). The upper phase of the solvent system was passed through the column until it just emerged from the bottom of the column. 100 mg. of the pooled BSP material, dissolved in 4 ml. of the upper phase of the solvent system, was applied to the column and eluted with the upper phase at a flow rate of 40 ml/hr. 10 ml. eluate fractions were collected and analyzed for homogeneity on thin layer chromatography (TLC) plates (0.25 mm. thick pre-coated EM Laboratories Inc. silica gel 60 plates) using a 1-butanol:pyridine:acetic acid:water (6:6:1.2:4.8) solvent system. Pooled fractions 52–66 produced 18 mg. of a substance which showed only one major component on TLC and which demonstrated gonadostatin activity in bioassay.

The components of the partition-chromatography-purified material obtained from the pooled 52–66 fractions were finally separated by reverse-phase HPLC using a Beckman Model 322 liquid chromatography system consisting of two model 100 A pumps, a model 420 microprocessor and a model 210 sample injection valve. Batch-wise purification of 15 mg. of the sample was done on a 0.46×25 cm. Spheri-5 Cyano (5 µm.) reverse phase liquid chromatography column protected with an 0.46×3.0 cm. Spheri-5 Cyano (5 µm.) guard column (Brownlee Labs). The column was eluted at 0.6 ml/min. with a pyridine:formic acid:1-propanol:water mobile phase of continuously decreasing polarity through increasing 1-propanol concentration, in which buffer A (1.5% formic acid, 1% pyridine in water) was continuously replaced by buffer B (1.5% formic acid, 1% pyridine, 60% 1-propanol in water). Five percent of the eluate was diverted to a fluorescamine detection system for determining the discharge of peptides from the column while the remainder of the eluate was collected in 2.4 ml. fractions. The major fluorescent peak eluted in fractions 24–31 which were pooled and subsequently found by bioassary to contain the gonadostatin activity.

EXAMPLE II

The protein nature of gonadostatin is demonstrated by its inactivation with trypsin.

Three hundred micrograms of gonadostatin at the point in the purification process of EXAMPLE I following the partition chromatography was digested in 30 µg. trypsin (Calbiochem) in 200 ml. 2% NH$_4$HCO$_3$ at 37° C. for 18 hours. The trypsin was then inactivated with 100 mg. soybean trypsin inhibitor (Sigma). After adding 100 mg. BSA, the samples were lyophilized for bioassay.

Bioassays of the digested material as well as the non-digested material are then carried out using the procedure described hereinbefore. Varying amounts of a known LRF-antagonist are included to verify the accuracy of the system. The results are summarized in the following table:

TABLE

| Treatment | LH (ng/ml) | FSH (ng/ml) |
|---|---|---|
| (1) Control | 367 ± 91 | 163 ± 33 |
| (2) LRF 1.25 ng | 3109 ± 105 | 1129 ± 43 |
| (3) LRF 1.25 ng + [D-Phe$^2$, D-Trp$^6$]-LRF 80 ng | 704 ± 52 | 288 ± 1 |
| (4) LRF 1.25 ng + [D-Phe$^2$, D-Trp$^6$]-LRF 40 ng | 1417 ± 123 | 548 ± 6 |
| (5) LRF 1.25 ng + BSP 300 µg. | 1372 ± 157 | 433 ± 60 |
| (6) LRF 1.25 ng + BSP 300 µg. (digested) | 2889 ± 164 | 1049 ± 141 |

It can be seen by comparison of the sample incubated with the LRF challenge dose (line 2) with the control sample (line 1) that the addition of LRF induces substantial secretion of both LH and FSH. The known LRF antagonist [D-Phe$^2$, D-Trp$^6$]-LRF suppresses LRF-induced LH and FSH secretion, as best seen by comparison of the samples incubated both with the LRF challenge dose plus a dose of the antagonist (lines 3 and 4) with the samples incubated only with the LRF challenge dose (line 2). Gonadostatin acts similarly to the LRF antagonist in inhibiting the LRF-induced secretion of LH and FSH, as can be seen by comparing the sample containing purified BSP peptide and the LRF challenge dose (line 5) with the LRF challenge dose sample (line 2). However, after digestion with trypsin, the inhibitory properties of gonadostatin are lost, as can be seen from the substantially identical induced LH and FSH secretions resulting from the LRF challenge dose plus trypsin-digested sample (line 6) and from the LRF challenge dose sample (line 2).

EXAMPLE III

The effects of administration of varying amounts of the finally purified BSP gonadostatin on LRF-induced pituitary secretion of gonadotropins is demonstrated by the assays summarized in graphs A and B. Rat anterior pituitary (RAP) cultures were co-incubated in culture wells for four hours with various amounts of BSP, LRF, and the LRF antagonist. Each culture well contained the cells from approximately one-quarter of a rat anterior pituitary.

Graph A summarizes the effects of various amounts of gonadostatin on LRF-induced LH production when gonadostatin and a challenge dose of LRF are co-incubated with RAP culture. A 1.25 ng. challenge dose of LRF is incubated with the RAP culture and with varying amounts of either gonadostatin or LRF antagonist for a period of four hours. Graph B represents the FSH levels produced in the same assays. In each case, the straight upper line represents the amount of the gonadotropin (LH or FSH) secreted as a result of the LRF challenge dose, and the straight broken line represents the basal level of secretion without addition of LRF.

As can be seen from graphs A and B, small doses of gonadostatin inhibit the LRF-induced secretion of the gonadotropins LH and FSH. The inhibitory effect of gonadostatin increases with the increasing amount of the dose, up to a dose of about 40 μg. whereas the LRF-induced LH or FSH secretion is at the lowest concentration with respect to the test. At higher dosages of gonadostatin, the inhibitory effect of gonadostatin lessens, until at a dosage of about 200 μg. or above, gonadostatin shows a stimulating effect upon the LRF-induced secretion.

EXAMPLE IV

Bioassays similar to those reported in EXAMPLE III were carried out except that RAP cultures were pre-incubated with BSP gonadostatin for 24 hours prior to the four-hour incubation period during which the incubation was continued with the challenge dose, 1.25 ng. LRF. The LH secretion of the various cultures is represented by graph C, and the FSH secretion by graph D.

It can be seen from graphs C and D that low levels of gonadostatin have no significant effect on the basal level of LH or FSH secreted by pituitary tissue in vitro. Dosages of BSP gonadostatin from about 10 μg. to about 40 μg. show an increasing inhibition of LRF-induced LH and FSH secretion, similar to that reported in EXAMPLE III. As the dosage of gonadostatin is increased above this level, the inhibiting effect of gonadostatin on LRF-induced LH and FSH secretion begins to fall off. At a dosage of gonadostatin above about 80 μg., stimulation of LH and FSH secretion takes place.

Complete characterization of gonadostatin has not been completed and hence the gonadostatin may best be characterized by its function. Gonadostatin is a proteineous natural substance produced by the gonads which selectively inhibits pituitary secretion of LH and FSH when administered in vitro in doses of about 10 to 40 μg. BSP gonadostatin has a molecular weight of about 11,000, as measured by gel filtration, and is a single-chain peptide having internal disulfide bonds. In bioassays using in vitro RAP cultures, gonadostatin, in a dosage of less than about 40 μg. per one-quarter of an RAP, inhibits LRF-induced LH and FSH secretions while gonadostatin at a dose above about 200 μg. stimulates RAP hormonal secretion. Gonadostatin is believed to have a relatively long biological half-life and as such may be valuable for making fine adjustments to pituitary secretions.

The precise amino acid sequence of bovine gonadostatin remains for further study, and when the structure is known, work may begin in artifically producing gonadostatin. It is believed that stepwise protein synthesis of gonadostatin on a commercial scale would be impractical with present methods; recombinant DNA techniques could be useful in producing gonadostatin. Continuing extraction and purification of BSP gonadostatin will make it possible to more carefully study its in vivo activity and more fully characterize the hormonal response system which regulates gonadal activity. The efficient extraction is made possible by the use of partition chromatography, following gel filtration and prior to HPLC. The disclosed extraction sequence is considered to provide the basis for a commercial separation process.

Gonadostatin is the first purified, natural substance which is known to act as an LRF antagonist, and although gonadostatin is sufficiently active for administration at a purity of about 80%, it preferably should have a purity of at least about 95% relative to other peptides present. It is known that LRF antagonists may be administered to mammalian animals to inhibit the LRF-induced secretion of LH and FSH. Reduced secretion of LH and FSH results in decreased steroid production by the gonads which in turn results in decreased fertility. Decreased fertility in the female may take the form of inhibition of ovulation, prevention of implantation of fertilized eggs, or resorption of fertilized eggs. In this respect, it is anticipated that effective dosages of gonadostatin would be administered in the range of about 0.1 to about 800 mg. per Kg. of body weight. Sufficiently reduced secretion of steroids will result in decreased levels of spermatogenesis in the male mammal. Because gonadostatins are naturally produced substances, they would not be expected to produce undesirable side reactions when administered to mammalians, particularly the species from which they are obtained.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 2 to about 200 micrograms of the peptide per kilogram of the body weight of the host.

While the invention has been described in terms of certain preferred embodiments, modifications obvious to one with ordinary skill in the art may be made without departing from the scope of the invention. For example, although the gonadostatin described was obtained from bovine gonadal secretions, gonadostatin is generally produced by mammalian animals and can be obtained from other mammals by similar procedures. It is also believed that fragments of the peptide gonadostatin may likewise display biological activity, and such fragments are considered to be within the scope of the invention. The conditions might be varied somewhat and still result in a substantially pure form of gonadostatin, and such variations are to be considered within the scope of the invention.

Various features of the invention are set forth in the following claims.

What is claimed is:

1. A method of deriving substantially pure gonadostatin, a proteinaceous mammalian gonadal substance characterized by its selective inhibition of LRF-stimulated pituitary secretions of LH and FSH in dosages below a threshold level and general stimulation of pituitary hormone secretion in dosages above a threshold level, the method comprising:

obtaining a mammalian gonadal secretion;

initially separating the components of said secretion according to molecular weight by gel filtration and obtaining a partially purified material containing eluate fractions which deomonstrate gonadostatin activity;

further separating components of said partially purified material by partition chromatography with a two-phase 1-butanol, pyridine, acetic acid, water eluent system to obtain further purified material; and additionally purifying said further purified material by reverse phase high performance liquid chromatography with a formic acid, pyridine, 1-propanol, water eluent system of increasing 1-propanol concentration to obtain a substantially purified substance which demonstrates activity in inhibiting the LRF-stimulated secretion of LH and FSH by the pituitary.

2. A method according to claim 1 wherein said gel filtration eluent fractions are selected for containing material having molecular weights of approximately 10,000 to 12,000 as determined by gel filtration.

3. A method according to claim 1 wherein the step of partition chromatography comprises:

forming a two-phase eluent system of 1-butanol, pyridine, acetic acid and water;

packing a column of highly cross-linked polysaccharide support material and equilibrating said support material with the lower phase of said eluent system; and eluting said partially purified material with the upper phase of said eluent system.

4. A method according to claim 1 wherein said eluent system comprises 1-butanol, pyridine, acetic acid and water in about a 6:6:1.2:4.8 ratio.

5. A proteinaceous mammalian gonadal substance derived by the method of claim 1, said substance characterized as having a molecular weight of approximately 10,000 to 12,000, as determined by gel filtration, and by its selective inhibition of LRF-stimulated pituitary secretions of LH and FSH in dosages below a threshold level and general stimulation of pituitary hormone secretion in dosages above a threshold level.

* * * * *

UNITED STATES PATENT AND TRADEMARK OFFICE
CERTIFICATE OF CORRECTION

PATENT NO. : 4,409,139

DATED : October 11, 1983

INVENTOR(S) : Ling et al.

It is certified that error appears in the above-identified patent and that said Letters Patent is hereby corrected as shown below:

Column 1, as an initial paragraph, insert:

"This invention was made with Government support under Contract HD09690 awarded by DHHS. The Government has certain rights in this invention".

Column 3, line 18, after "acid", insert a comma (,).

Column 4, line 1, correct the spelling of "bioassay".

Column 5, lines 45-46, correct the spelling of "proteinaceous",

Column 5, line 62, correct the spelling of "artificially".

Column 7, line 17, correct the spelling of "demonstrate".

Signed and Sealed this

Twenty-seventh Day of March 1984

[SEAL]

Attest:

GERALD J. MOSSINGHOFF

Attesting Officer  Commissioner of Patents and Trademarks